United States Patent
Cerff et al.

(10) Patent No.: US 6,194,201 B1
(45) Date of Patent: Feb. 27, 2001

(54) EXPRESSION SYSTEM FOR ANAEROBIC GENE EXPRESSION IN HIGHER PLANTS

(75) Inventors: Rüdiger Cerff, Braunschweig; Klaus Düring, Frechen; Reinhard Hehl, Braunschweig, all of (DE); Uwe Köhler, Cambridge (GB)

(73) Assignee: MPG Cologne GmbH Molecular Plant & Protein Biotechnology, Cologne (DE)

( * ) Notice: Subject to any disclaimer, the term of this patent is extended or adjusted under 35 U.S.C. 154(b) by 0 days.

(21) Appl. No.: 09/091,693

(22) PCT Filed: Dec. 17, 1996

(86) PCT No.: PCT/DE96/02428

§ 371 Date: Oct. 27, 1998

§ 102(e) Date: Oct. 27, 1998

(87) PCT Pub. No.: WO97/22707

PCT Pub. Date: Jun. 26, 1997

(30) Foreign Application Priority Data

Dec. 19, 1995 (DE) ............................... 195 47 272

(51) Int. Cl.[7] ............................. C12N 5/04; C12N 15/56; C12N 15/82; C12N 15/90; A01H 5/00

(52) U.S. Cl. .................. 435/320.1; 435/69.1; 435/468; 435/206; 536/24.1; 800/278; 800/301; 800/302; 800/317.2; 800/320.2; 800/320.1; 800/306; 800/312; 800/313; 800/314; 800/317.4; 800/279; 800/283; 800/284; 800/288

(58) Field of Search ............................. 435/69.1, 320.1, 435/410, 417, 418, 419, 468, 206; 536/24.1, 23.6; 800/278, 279, 283, 284, 288, 295, 298, 301, 302, 317.2, 320.2, 312, 313, 314, 306, 317.4, 320.1

(56) References Cited

FOREIGN PATENT DOCUMENTS 0 278 658 A2   8/1988   (EP) .............................. C12N/15/00

OTHER PUBLICATIONS

Melchers et al, Plant Mol. Biol., vol. 21, pp. 583–593, 1993.*
Niebel et al, MPMI, vol. 8, pp. 371–378, 1995.*
Broglie et al, Phil. Trans. R. Soc. Lond. B, vol. 342, pp. 265–270, 1993.*
Baulcombe et al, Trends Genet., vol. 5, pp. 56–60, 1989.*
Bulow et al, MPMI, vol. 12, pp. 182–188, 1999.*
Kim et al, Plant Mol. Biol., vol. 24, pp. 105–117, 1994.*
Gardner, R.C., Sci. Hort., vol. 55, pp. 65–82, 1993.*
Russel et al, Plant Physiol., vol. 99, pp. 615–620, 1992.*
Kohler et al, Plant Mol. Biol., vol. 29, pp. 1293–1298, 1995.*
Rumeau et al, Plant Physiol., vol. 93, pp. 1134–1139, 1990.*
Vaeck et al, Nature, vol. 328, pp. 33–37, 1987.*
Bucher et al, EMBO J., vol. 13, pp. 2755–2763, 1994.*
Bradford, "A Rapid and Sensitive Method for the Quantitation of Microgram Quantities of Protein Utilizing the Principle of Protein–Dye Binding," *Anal. Biochem.* 72:248–254 (1976).
Dolferus, et al., "Differential Interactions of Promoter Elements in Stress Responses of the *Arabidopsis Adh* Gene," *Plant Physiol.*—105:1075–1087 (1994).
Düring, et al., "Transgenic Potato Plants Resistant to the Phytopathogenic Bacterium *Erwinia Carotovora*," *The Plant Journal*—3(4):587–598 (1993).
Ellis, et al., "Maize Adh–1 Promoter Sequences Control Anaerobic Regulation: Addition of Upstream Promoter Elements from Constitutive Genes is Necessary for Expression in Tobacco," *The EMBO Journal*—6(1):11–16 (1987).
Fischer, et al., "Plant Disease Resistance Resulting from the Expression of Foreign Phytoalexins," *Current Opinion in Biotechnology*—5:125–130 (1994).
Flading, "Transformation of Diploid and Tetraploid Potato Clones with the Rol C Gene of *Agrobacterium Rhizogenes* and Characterization of Transgenic Plants," *Plant Breeeding*—104:295–304 (1990).
Honma, et al., "High–Frequency Germinal Transposition of $Ds^{ALS}$ in Arabidopsis," *Proc. Natl. Acad. Sci.*—90:6242–6246 (1993).
Jefferson, et al., "GUS Fusions: β–Glucuronidase as a Sensitive and Versatile Gene Fusion Marker in Higher Plants," *The EMBO Journal*—6(13):3901–3907 (1987).
Kersanach, et al., "Five Identical Intron Positions in Ancient Duplicated Genes of Eubacterial Origin," *Letters to Nature*—367:387–389 (1994).
Kyozuka, et al., "Anaerobic Induction and Tissue–Specific Expression of Maize *Adh1* Promoter in Transgenic Rice Plants and their Progeny," *Mol. Gen. Genet.*—228:40–48 (1991).
Yang, et al., "Stress Responses and Metabolic Regulation of Glyceraldehyde–3–Phosphate Dehydrogenase Genes in Arabidopsis," *Plant Physiol.*—101:209–216 (1993).
Zhu, et al., "Enhanced Protection Against Fungal Attack by Constitutive Co–Expression of Chitinase and Glucanase Genes in Transgenic Tobacco" *Bio/Technology*—12:807–812 (1994).

\* cited by examiner

*Primary Examiner*—David T. Fox
*Assistant Examiner*—Ashwin D. Mehta
(74) *Attorney, Agent, or Firm*—Albert T. Halluin; Viola T. Kung; Howrey Simon Arnold & White, LLP

(57) ABSTRACT

The present invention relates to an expression system for anaerobic gene expression in higher plants. The expression system comprises the promoter GapC4 or a fragment or variant and a gene to be expressed. A concrete field of application of the present invention is agriculture, particularly resistance cultivation.

9 Claims, No Drawings

EXPRESSION SYSTEM FOR ANAEROBIC
GENE EXPRESSION IN HIGHER PLANTS

FIELD OF THE INVENTION

The present invention relates to an expression system for anaerobic gene expression in higher plants. A concrete field of application of the present invention is agriculture, particularly resistance cultivation and the increase in the efficiency of useful plants.

BACKGROUND OF THE INVENTION

The loss of harvested crops, which results from diseases of plants, represents a world-wide problem. For example, potatoes suffering from potato wet rot or potato rot (rotting of the tuber) and black leg or black stem (rotting of the lower stem sections) after infection by the phytopathogenic bacterium *Erwinia carotovora*, results in crop losses to an estimated amount of 100 million dollars world-wide (Pérombelon et al., 1980, *Ann. Rev. Phytopathol.* 18: 361–387). There is a number of studies dealing with the transmission of resistance factors to plants by means of genetic engineering (Lamb et al., 1992, *Bio/Technology* 10: 1436–1445; Hain et al., 1994, *Current Opinion in Biotechnology*, 125–130; Zhu et al., 1994, *Bio/Technology* 12: 807–812). In order to increase the resistance of potatoes to *Erwinia carotovora*, the T4 lysozyme gene of the bacteriophage T4 was expressed in transgenic potatoes (Düring et al., 1993, *Plant J.* 3: 587–598).

However, since bacterial diseases of plants often spread under anaerobic conditions, the resistance factors for plants transmitted so far, are effective only in a very restricted extent. This applies particularly to the above-mentioned disease of potatoes suffering from potato rot and black leg, since the infection caused by *Erwinia carotovora* takes place predominantly under anaerobic conditions. This effect is increased by the formation of a mucus from bacteria and degradation products of vegetable cell membranes. Regarding an effective expression of an antibacterial protein under optimum conditions, it is desirable to control the corresponding foreign gene by a promoter active under these conditions.

Three anaerobic promoters have been tested in transgenic plants so far. These are the Adh1 promoter from corn, the Adh promoter from *Arabidopsis thaliana* and the GapC promoter from *Arabidopsis thaliana*. The Adh1 promoter from corn was investigated in tobacco and rice (Ellis et al., 1987, *EMBO J.* 6: 11–16; Kyozuka et al., 1991, *Mol. Gen. Genet.* 228: 40–48). The GapC promoter from Arabidopsis was investigated in tobacco (Yang et al., 1993, *Plant Physiol.* 101: 209–210), and the Adh promoter from Arabidopsis was investigated in Arabidopsis as such (Dolferus et al., 1994, *Plant Physiol.* 105: 1075–1087). It turned out that all promoters convey only 2 to 81 times the induction of the reporter gene over the background and are not active in all of the tissues.

SUMMARY OF THE INVENTION

One objective of this invention to achieve the expression of resistance factors in useful plants and to produce corresponding transgenic plants. It is a further object of this invention to achieve the anaerobic expression of the T4 lysozyme gene in potatoes and produce corresponding transgenic plants. A specific object consists in making potatoes resistant to phytopathogenic bacteria.

The present invention is achieved by an expression system comprising the GapC4 promoter or parts or variants of the GapC4 promoter and a gene to be expressed.

DETAILED DESCRIPTION OF THE INVENTION

According to the invention, genes for an antibacterial protein, particularly for a T4 lysozyme, resistance genes (r-determinants) against viruses, nematodes, bacteria and fungi, genes having an insecticidal effect, glycolysis-increasing genes and fermentation-increasing genes are provided.

According to the invention, the expression system is applied to an anaerobic gene expression in higher plants. It is used preferably in cultivated plants such as potatoes, rice, grain, corn, tomatoes, brassicaceae, leguminous plants, cotton, sugar beets and carrots.

This invention also relates to higher plants, preferably transgenic cultivated plants such as potatoes, rice, grain, corn, tomatoes, brassicaceae, leguminous plants, cotton, sugar beets and carrots, which contain the expression system according to the invention.

Transgenic potatoes that contain an expression system from a GapC4 promoter and the gene for a T4 lysozyme are of special importance.

The major advantage of the GapC4 promoter used according to the invention (GenBank accession No. L40803) consists in that it has an induction profile excellently suited for the objective. The anaerobic expression achieves the intensity of the 35S promoter of cauliflower mosaic virus (35S CaMV) which is frequently used under aerobic conditions for the expression of foreign genes. Furthermore, the promoter is active in all tissues such as the flower or blossom, leaf and root. The anaerobic induction of the GapC4 promoter has not been known neither in plants nor in a transient expression system. Surprisingly, the promoter is especially active in cultivated potatoes.

Additionally, there are other potential applications of the invention. Another problem is represented, especially in moist climate, by periodic flooding of fields, which may lead to crop failure. As they are aerobic organisms, plants cannot survive prolonged periods of extensive moisture which results in a decrease of oxygen available to the plants (Perata and Alpi, 1993, Plant Sci. 93, 1–17). The tolerance of plants towards insufficient oxygen supply differs rather widely for individual species. For example, the embryo in rice calyopsis also germinates under these conditions without any difficulties, whereas corn germs survive without oxygen for only about 24 hours. A general adaptive strategy of higher plants to anaerobic conditions is the increase in glycolysis as well as the starting of fermentation processes. In order to increase the tolerance of plants towards insufficient oxygen supply, the genes which take part in glycolysis as well as fermentation can be controlled by an anaerobically inducible promoter. These genes are then expressed in the case of insufficient oxygen supply.

The present invention is explained in more detail below by way of the examples. However, the intention is not intended to be limited thereby as the examples are merely illustrative.

DETAILED DESCRIPTION OF THE PREFERRED EMBODIMENTS

EXAMPLE

In order to investigate whether the GapC4 promoter is induced anaerobically in potatoes, and induced after infection with *Erwinia carotovora*, GapC4 promoter-reporter gene constructs are transformed into potatoes. Following the infection of the transgenic potatoes with *Erwinia carotovora* and the incubation of tissues of the transgenic potatoes under anaerobic conditions, the reporter gene expression can be measured. The reporter gene can then be replaced is vitro by the T4 lysozyme gene and transformed into the potatoes. Thereafter, the transgenic potatoes are investigated for increased resistance to *Erwinia carotovora*.

The reporter gene constructs were constructed as described below. All agrobacterium T-DNA constructs are based on the binary vector pOCA28 (Honma et al., 1993, *Proc. Natl. Acad. Sci., USA* 90: 6242–6246; Olszewski et al., 1988, *Nucleic Acids Res.* 16: 10765–10782). Plasmids pUK443, assession number DSM 13719, deposited Sep. 4, 2000 (DSMZ-DEUTSCHE SAMMLUNG VON MIKRO-ORGANISMEN UND ZELLKULTUREN GmbH, Mascheroder Weg 1b, D-38124 Braunschweig), and pUK444, assession number DSM 13724, deposited Sep. 14, 2000 (DSMZ-DEUTSCHE SAMMLUNG VON MIKRO-ORGANISMEN UND ZELLKULTUREN GmbH, Mascheroder Weg 1b, D-38124 Braunschweig), carrying 785 base pairs of the GapC4 promoter and 461 base pairs thereof, respectively, the first intron of the GapC4 gene as well as the β-glucuronidase reporter gene were used for T-DNA constructs. In order to exclude possible negative effects of the GapC4 intron from corn in transgenic tobacco plants and potatoes, the intron was cut out of the plasmids pUK443 and pUK444 by restriction digestion using enzymes Xhol and Ncol. Following an anaplerotic reaction of the ends resulting from restriction digestion, the pUK403 and pUK404 plasmids without introns were produced. The promoter-reporter gene fragments of these plasmids were cut out by Pvull digestion and cloned into the Smal restriction site of pOCA28. The resulting pOCA28 derivatives, pUK4030, 4040 and 4041, carry the GapC4 promoter-reporter gene construct. The β-glucuronidase reporter gene without promoter was cloned into pOCA28 as a control. pUK4030 and 4040 carry the reporter gene constructs with the promoter being proximal relative to the right-hand T-DNA border sequence. In pUK4041, the reporter gene is oriented differently.

All of the recombinant DNA techniques are carried out according to standard protocols (Sambrook et al., 1989, Molecular cloning, A Laboratory Manual. New York: Cold Spring Harbor Laboratory Press). For cloning the T4 lysozyme gene, the β-glucuronidase reporter gene can be removed from plasmids pUK403 or 404 by restriction digestion, and the T4 lysozyme gene can be cloned into the plasmids instead. The T4 lysozyme gene controlled by the GapC4 promoter is recloned into an Agrobacterium T-DNA vector. Following introduction into *Agrobacterium tumefaciens*, all constructs are transformed into the potatoes according to standard protocols (Düring et al., 1993, *Plant J.* 3: 587–598; Fladung, 1990, *Plant Breeding* 104: 295–304). Transgenic potatoes are selected by means of an antibiotic resistance gene on the T-DNA and investigated for expression of the introduced β-glucuronidase reporter gene and the T4 lysozyme gene under anaerobic conditions as well as after infection with *Erwinia carotovora*.

For the purpose of anaerobic induction, plant tissue is incubated in an air-tight glass container (Merck) together with Anaerocult A (Merck) for at least 12 hours. For the fluorimetric GUS assay, the plant material is homogenized and incubated with the β-glucuronidase substrate 4-methylumbelliferyl-β-D-glucuronidase (MUG) at 37° C. Fluorescence quantification is carried out according to Jefferson et al., 1987, *EMBO J.* 6: 3901–3907 and protein concentrations are determined according to Bradford, 1976, *Anal. Biochem.* 7: 248–254. In order to measure the tissue specificity of the reporter gene expression, the intact anaerobically induced plant material is infiltrated in vacuo with a solution of 1 mM X-Gluc (5-bromo-4-chloro-3-indolyl-β-D-glucuronic acid) and incubated at 37° C. overnight. For making the staining or coloring better visible, the chlorophyll is extracted using 70% ethanol (Jefferson, supra).

In order to measure the expression of the T4 lysozyme gene, Northern blot analyses are carried out using a T4 lysozyme-specific probe after anaerobic incubation of the tissue. Whole RNA is isolated by means of the RNeasy kit (Qiagen). The concentration of the RNA is detennined photometrically, and 10 micrograms of the RNA are placed in a lane on a 1% agarose gel containing formaldehyde. Following electrophoresis, the RNA is blotted from the gel onto nitrocellulose or nylon membranes (Amersham) using 0.05 N NaOH as transfer buffer (Sambrook et al., supra). The T4 lysozyme-specific probe is marked and hybridized with the RNA filter according to standard conditions (Sambrook et al., supra, Düring et al., supra).

After confirmation of the anaerobic induction of reporter gene and T4 lysozyme gene, investigations are made as to whether both genes are induced even after the infection by the phytopathogenic bacterium *Erwinia carotovora* and whether the T4 lysozyme gene is activated under the control of the GapC4 promoter such that it conveys resistance. The induction of the reporter gene and T4 lysozyme gene is determined as described above. For this purpose, the tuber or bulb material underneath the macerated tissue is utilized.

The infection test is carried out with a pathogenic strain of *Erwinia carotovora* ssp. *atroseptica* or ssp. *carotovora* in plastic containers in the absence of air. Slices having a defined size are produced from potato tubers and are inoculated in the middle with a defined number of bacterial cells in a freshly cut state in a small volume. Incubation takes place in plastic containers having a water layer on the bottom on a soaked filter paper. As a result, saturated humidity will be achieved. The bacterial growth is traced by means of tissue maceration and the resulting bacterial mucus. Because of the bacterial mucus that forms, potato cells are covered in an air-tight fashion. As a function of the inoculin density, the extent of maceration is determined after a defined period of time. The relative decrease of susceptibility can be determined in comparison with control explants.

As an alternative, eye cuttings infected with bacteria can be pricked out and cultivated in a greenhouse under moist or humid conditions. Lack of oxygen results from silting of the earth, which supports the multiplication of the bacteria. The number of accumulated healthy sprouts is determined in comparison with the control explants. The extent of reduced susceptibility can be determined by this.

What is claimed is:

1. An expression system for expressing a non-native gene under anaerobic conditions in plants, comprising the promoter GapC4 or a fragment thereof and a gene to be expressed.

2. The expression system according to claim 1 wherein the gene encodes for an antibacterial protein.

3. The expression system according to claim 2, wherein the gene encodes for T4 lysozyme.

4. The expression system according to claim 1, wherein the gene is a resistance gene (r-detenninant) and wherein the gene confers resistance against one or more agents selected from the group consisting of viruses, nematodes, bacteria and fungi.

5. The expression system according to claim 1, wherein the gene has an insecticidal effect.

6. The expression system according to claim 1, wherein the gene is a glycolysis-increasing gene.

7. The expression system according to claim 1, wherein the gene is a fermentation-increasing gene.

8. The expression system according to claim 1 wherein the plants are selected from the group consisting of potatoes, rice, grain, corn, tomatoes, brassicaceae, leguminous plants, cotton, sugar beets and carrots.

9. Transgenic potatoes containing an expression system comprising a GapC4 promoter and a gene encoding a T4 lysozyme.

* * * * *

UNITED STATES PATENT AND TRADEMARK OFFICE
CERTIFICATE OF CORRECTION

PATENT NO. : 6,194,201 B1
DATED : February 21, 2001
INVENTOR(S) : Rüdiger Cerff, et al.

It is certified that error appears in the above-identified patent and that said Letters Patent is hereby corrected as shown below:

Column 3,
Line 4, change "is" to -- in --

Column 4,
Line 11, change "detennined" to -- determined --

Signed and Sealed this

Eighteenth Day of September, 2001

Attest:

*Nicholas P. Godici*

NICHOLAS P. GODICI
*Attesting Officer*         *Acting Director of the United States Patent and Trademark Office*